United States Patent [19]

Havens et al.

[11] Patent Number: 5,153,075
[45] Date of Patent: * Oct. 6, 1992

[54] PERMANENT ANTISTATIC ACID COPOLYMER/QUATERNARY AMINE POLYMERIC FILMS

[75] Inventors: Marvin R. Havens, Greer, S.C.; William P. Roberts, Columbia, Md.

[73] Assignee: W. R. Grace & Co.-Conn., Duncan, S.C.

[*] Notice: The portion of the term of this patent subsequent to Mar. 12, 2008 has been disclaimed.

[21] Appl. No.: 558,043

[22] Filed: Jul. 25, 1990

Related U.S. Application Data

[60] Division of Ser. No. 249,488, Sep. 26, 1988, Pat. No. 4,999,252, which is a continuation-in-part of Ser. No. 143,885, Jan. 14, 1988, abandoned.

[51] Int. Cl.$^5$ ............................................. B32B 27/08
[52] U.S. Cl. ..................... 428/516; 260/DIG. 20; 260/DIG. 21; 428/520
[58] Field of Search ............... 428/500, 516, 520, 515; 525/329.9 N, 379, 380

[56] References Cited

U.S. PATENT DOCUMENTS

| | | |
|---|---|---|
| T961,009 | 8/1977 | Hendy ................................. 427/401 |
| 2,236,515 | 4/1941 | Cahn et al. . |
| 3,022,543 | 2/1962 | Baird, Jr. et al. . |
| 3,236,881 | 2/1966 | Distler et al. . |
| 3,324,091 | 6/1967 | Savides . |
| 3,405,020 | 10/1968 | Chavannes ......................... 156/306 |
| 3,416,984 | 12/1968 | Chavannes et al. ................ 156/209 |
| 3,445,440 | 5/1969 | Susi et al. . |
| 3,517,045 | 6/1970 | Susi et al. . |
| 3,555,604 | 1/1971 | Pahlke . |
| 3,586,565 | 6/1971 | Fielding ............................ 156/210 |
| 3,732,196 | 5/1973 | Dieterich . |
| 3,741,253 | 6/1973 | Brax et al. ......................... 138/137 |
| 3,785,899 | 1/1974 | Fielding ............................ 156/209 |
| 3,821,182 | 6/1974 | Baird, Jr. et al. . |
| 3,894,077 | 7/1975 | Horikawa et al. . |
| 3,933,779 | 1/1976 | Baron et al. . |
| 4,048,428 | 9/1977 | Baird et al. ........................ 526/343 |
| 4,070,531 | 1/1978 | Schwarze et al. . |
| 4,104,175 | 8/1978 | Martinsson et al. . |
| 4,178,401 | 12/1979 | Weinberg et al. .................. 428/35 |
| 4,188,443 | 2/1980 | Mueller et al. ..................... 428/216 |
| 4,194,039 | 3/1980 | Mueller ............................... 428/213 |
| 4,229,241 | 10/1980 | Mueller ............................... 156/243 |
| 4,268,583 | 5/1981 | Hendy ................................. 428/516 |
| 4,274,900 | 6/1981 | Mueller et al. ..................... 156/229 |
| 4,433,113 | 2/1984 | Woodward . |
| 4,494,651 | 1/1985 | Malcolm ............................. 206/328 |
| 4,576,669 | 3/1986 | Caputo ................................ 156/145 |
| 4,579,516 | 4/1986 | Caputo ................................ 425/388 |
| 4,605,684 | 8/1986 | Pcolinsky, Jr. ..................... 521/107 |
| 4,623,594 | 11/1986 | Keough .............................. 428/500 |
| 4,678,836 | 7/1987 | McKinney et al. ................. 525/221 |

FOREIGN PATENT DOCUMENTS

| | | |
|---|---|---|
| 0206446 | 12/1986 | European Pat. Off. . |
| 0219315 | 4/1987 | European Pat. Off. . |
| 1559322 | 3/1969 | France . |
| 59-47243 | 3/1984 | Japan . |
| 54093025 | 10/1987 | Japan . |
| 1206273 | 1/1986 | U.S.S.R. . |
| 938729 | 10/1963 | United Kingdom . |
| 2010851 | 7/1979 | United Kingdom . |

OTHER PUBLICATIONS

"Antistatic Agents", Exxon Chemicals Americas, p A-6, Sept. 21, 1983.
"Polymer Preprints", vol. 29, No. 2, Sept. 1988.
Copolymers of Ethylene and Acryl Acids, pp. 21-23.
Permanent Antistatic Acid, vol. 1, pp. 196-197, 1972.

Primary Examiner—Christopher Henderson
Attorney, Agent, or Firm—William D. Lee, Jr.; Jennifer L. Skord; Mark B. Quatt

[57] ABSTRACT

An acid copolymer/quaternary amine mixture is disclosed which is permanently antistatic. The acid copolymer is a copolymer of (i) a major amount by mol % of an alpha-olefin of the formula $RCH=CH_2$ wherein R is H or $C_1$ to $C_8$ alkyl, and (ii) a minor amount by mol % of an alpha,beta-ethylenically unsaturated carboxylic acid. The quaternary amine is of the formula $[(R^1)(R^2)(R^3)(R^4)N]+$ $[X]-$ wherein $R^1$ is selected from H, aryl,-or $C_1$ to $C_{50}$ alkyl optionally having one or more non-contiguous $C=O$ or $NHC=O$ or —S— or —O— in the carbon chain, or the same as $R^2$; each of $R^2$, $R^3$, and $R^4$ is the same or different and selected from H, $C_1$ to $C_{18}$ alkyl optionally substituted with one or more OH or from $—(R^5—O)_a—H$ where a is an integer from 1 to 10 and $R^5$ is ethylene or propylene; and X is an anion selected from chloride, bromide, iodide, fluoride, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, citrate, trifluoroacetate, propionate, tartrate or carbonate.

3 Claims, No Drawings

PERMANENT ANTISTATIC ACID COPOLYMER/QUATERNARY AMINE POLYMERIC FILMS

This is a divisional application of copending application Ser. No. 249,488, filed on Sep. 26, 1988 now U.S. Pat. No. 4,999,252 which is a continuation-in-part of copending U.S. Ser. No. 143,885, filed Jan. 14, 1988, now abandoned.

This invention relates to an acid copolymer/quaternary amine mixture. The new, acid copolymer/quaternary amine mixtures of the invention are useful, for instance, in making film for packaging for electronic devices that are sensitive to static electricity. The film has permanent, non-bleeding antistatic characteristics. By "permanent, non-bleeding" antistatic characteristics is meant the film exhibits a static decay time (hereinafter abbreviated as SDT) under about 3000 milliseconds (hereinafter abbreviated as ms) when the static decay test using 5000 volts direct current (hereinafter abbreviated as Vdc) is conducted as per Federal Test Method 101c, Method 4046.1, after a 24-hour water shower, i.e. the antistat property is not washed out by the shower. In the preferred embodiments, the film will also still have this SDT of about 3000 ms or less even after 12 days in a hot (approximately 70° C.) oven.

BACKGROUND OF THE INVENTION

When two surfaces are brought in contact with each other, a transfer of electrons may occur resulting in a residual static electrical charge when the surfaces are separated. This phenomena is known as triboelectricity. If the surface is composed of a material that is a conductor, the electrons will dissipate quickly thereby eliminating the excess charge. On the other hand, if the surface is composed of a material that is an insulator (a dielectric), the surface charge takes much longer to dissipate. Thermoplastic polymers are typically excellent insulators and thus are unsatisfactory for uses requiring a nature that will dissipate charges. As the polymers accumulate high charges promoting an attraction for dust and dirt, they can discharge to any lower potential body with which they come in contact. To modify a polymer to have antistatic characteristics and dissipate charges, the conductivity might be increased which in turn causes an increase in the rate of static dissipation. This has been accomplished in the past by the use of antistatic agents to promote static-charge decay of surfaces thereby reducing clinging effect, eliminating spark discharge, and preventing accumulation of dust.

It is well known that static charge can be reduced by increasing the moisture content of the atmosphere, and thus the approach in the past has been to use an antistatic agent which will modify the inherently dielectric polymer to impart hydrophilic properties to it by providing functional groups that attract moisture to it. For instance, it is well known to apply external antistatic agents onto polymers by conventional coating or painting methods. Also, it is well known to employ internal antistatic agents which are volume dispersed by admixing in the polymer; i.e. incorporated into the polymer by compounding or extrusion prior to or during molding or film-forming operations, and which work by migrating to the polymer surface. This migration is colloquially referred to in the art of antistatic polymer technology as a "blooming" or "bleeding" effect. When the antistatic agent has not remained volume dispersed but instead has bloomed or bled to the surface, the mechanism for moisture attraction is the same as with the painted on external antistatic agents. The atmospheric moisture is attracted causing decay or dissipation of static charges, i.e. such films depend on ambient humidity. Accordingly a high rate of blooming is required. Such films can overbloom and lose their antistatic character if subjected to a 24 hour water shower or a prolonged heat exposure.

Many patents show quaternary amines (also referred to as quaternary ammonium compounds or salts) as antistatic agents. Examples are U.S. Pat. No. 3,324,091 to Sauides, U.S. Pat. Nos. 3,445,440, and 3,517,045 both to Susi and Arthen, U.S. Pat. No. 3,894,077 to Horikawa et al, U.S. Pat. No. 4,104,175 to Martinsson et al, U.S. Pat. No. 4,268,583 and T961009 both to Hendy, and U.S. Pat. No. 4,605,684 to Pcolinsky.

Also of interest is Japanese Published Patent Application Kokai No. 59-47243, Ito et al, assignors to Mitsui (published Mar. 16, 1984) which shows an electrically conductive resin composition comprising ethylene/alpha,beta unsaturated carboxylic acid copolymer and a tertiary alkanolamine.

More particularly, U.S. Pat. No. 3,933,779 issued Jan. 20, 1976 to Baron et al assignors to Fine Organics discloses an antistatic polymer blend comprising a synthetic polymer and an antistatically effective amount of a compound of the formula:

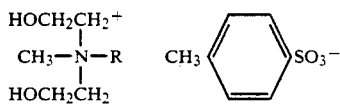

wherein R is alkyl of 4 to 18 carbon atoms unsubstituted or substituted by halo or aryl.

At pages 18 and 19 of published European Patent Application 0219315 Mott assignor to Dow, date of publication Apr. 22, 1987, is a passage stating that their preferred antistatic material is an acrylate monomer-oligomer mixture containing an alkylether triethyl ammonium sulfate available from Metallized Products under the trade-name Staticure, which material is curable by exposure to an electron beam to a permanent, non-bleeding coating which is not dependent on humidity for its antistatic effect. The passage in EP 0219315 goes on to say that further details concerning this material appear in British Patent Application No. 2,156,362 published Oct. 9, 1985.

British Patent Application No. 2,156,362 is the counterpart of U.S. Pat. No. 4,623,594 issued Nov. 18, 1986 to Keough assignor to Metallized Products. U.S. Pat. No. 4,623,594 claims:

1. An antistatic laminate, both sides of which have antistatic characteristics, comprising:
   (A) a substrate sheet;
   (B) a continuous coating on one side of said substrate sheet, said continuous coating comprising the electron radiation cured product of:
   (1) an electron beam curable prepolymer; and
   (2) an effective amount of a saturated quaternary ammonium compound antistatic agent soluble in said prepolymer the product being a reaction product of the prepolymer and the ammonium compound converted into a substantially solid product.

2. the antistatic laminate of claim 1 wherein said quaternary ammonium compound is a *trialkylalkyletherammonium* salt. [Emphasis supplied.]

The laboratory examples of U.S. Pat. No. 4,623,594 show that the particular trialkyl alkylether ammonium salt employed was Emerstat 6660 from Emery Industries. Page 52 of a catalog entitled "Miscellaneous Surfactants" describes Emerstat 6660 as a 100% active liquid cationic compound which offers high performance antistatic capacity, but page 52 does not give any generic chemical formula. It is believed that Emerstat 6660 is a diethoxylated alkyl ammonium salt of the formula $(A)(A')N[(CH_2CH_2O)_nH]_2^+ \; A'OSO_3^-$ which is further described below.

Of general interest is U.S. Pat. No. 4,678,836 (Jul. 7, 1987) McKinney et al assignors to Dow Chemical. It shows blends of linear low density polyethylene (LLDPE) and ethylene-acrylic acid (EAA).

SUMMARY OF THE INVENTION

The present acid copolymer/quaternary amine mixture may be made into a single ply and/or multiple ply film, and additional advantageous features such as tougher films, further described below, may be obtained when such films are irradiated by electron beam. The films of the invention will dissipate an applied charge of ±5000 volts direct current (Vdc) in about 3000 milliseconds (ms) or less, more preferably about 2000 ms or less. The films of the invention still will exhibit this static decay time behavior after a 24 hour water shower. In the preferred embodiments, the films also will still exhibit this static decay time behavior after 12 days in a hot (approximately 70° C.) oven. This is true even if the films were not previously irradiated by electron beam. Thus, the antistatic effect is permanent and non-bleeding, without any requirement for electron beam "curing". Accordingly, very satisfactory films may be obtained absent any electron beam irradiation. Thus the irradiation does not have to be employed but may be employed if desired to achieve enhanced toughness and the like as further described below. The new, acid copolymer/quaternary amine mixture may be molded or extruded alone or together with polymers known for their strength such as ethylene vinyl acetate (EVA), polypropylene (PP) or linear low density polyethylene (LLDPE). The resultant film is useful for making packaging, such as a bag or over-wrap, for electronic devices that are sensitive to static electricity. If desired, the packaging could be a heat-shrinkable or vacuum skin packaging. Such a film may also be fashioned to have cushioning characteristics by using bubble cap (also known as air cushioning) machinery such as that described in U.S. Pat. Nos. 4,576,669 and 4,579,516 both to Caputo, or that described in U.S. Pat. Nos. 3,416,984, 3,405,020, 3,586,565, and 3,785,899, all assigned to Sealed Air, the disclosures of which are incorporated herein by reference, to make a bubble cap package which provides cushioning and then bagging or wrapping an electronic device therewith. Such a cushioning bubble cap material (also known as cellular material or air cushioning material) is also useful in lining a portable work station used for storage and transportation of static electricity sensitive devices such as the work stations disclosed in U.S. Pat. No. 4,494,651 issued in 1985 to Malcolm. Also such a film, which may or may not be in a cushion form, is useful to make a package for devices in a medical operating room where explosive oxygen and/or ether are present and thus protection from static electricity must be provided. Also such films may be advantageously employed for any use requiring a plastic with a decreased tendency to accumulate dust.

Therefore, it is an object of the present invention to provide a novel, antistatic acid copolymer/quaternary amine mixture useful in making a film useful for wrapping static sensitive devices. It is also an object to provide such films having an increased tendency to dissipate electrostatic charges. It is also an object that the films are substantially independent of ambient humidity, i.e. the films are still able to decay an applied ±5000 VDC in less than about 3000 ms, more preferably less than about 2000 ms, when conditioned at less than about 15% relative humidity.

A feature of the films is that they also have excellent see-through properties which is advantageous for reading code numbers preprinted on a product wrapped with the film.

The present invention provides an acid copolymer/quaternary amine mixture comprising (A) a polymer containing carboxylic acid moieties and (B) an antistatically effective amount of a quaternary amine wherein:
(A) the polymer containing carboxylic acid moieties is a copolymer of (i) a major amount by mol % of an alpha-olefin of the formula $RCH=CH_2$ wherein R is H or $C_1$ to $C_8$ alkyl, and (ii) a minor amount by mol % of an alpha,beta-ethylenically unsaturated carboxylic acid, and
(B) the quaternary amine is of the formula

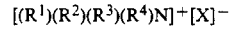

$$[(R^1)(R^2)(R^3)(R^4)N]^+[X]^-$$

wherein
$R^1$ is selected from H, aryl, $C_1$ to $C_{50}$ alkyl optionally having one or more non-contiguous $C=O$ or $NHC=O$ or $—S—$ or $—O—$ in the carbon chain, or the same as $R^2$;
each of $R^2$, $R^3$, and $R^4$, is the same or different and selected from H, $C_1$ to $C_{18}$ alkyl optionally substituted with one or more OH or from $—(R^5—O)_a—H$ where a is an integer from 1 to 10 and $R^5$ is ethylene or propylene; and
X is an anion selected from chloride, bromide, iodide, fluoride, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, trifluoroacetate, citrate, propionate, tartrate or carbonate. The present invention also provides for a film comprising this mixture.

Preferably, the $C_1$ to $C_8$ alkyl phosphate is methyl phosphate or ethyl phosphate, the $C_1$ to $C_8$ alkyl sulfate is methyl sulfate or ethyl sulfate, and the $C_1$ to $C_8$ alkyl or $C_6$ to $C_{24}$ alkaryl or aryl sulfonate is methanesulfonate, butanesulfonate, benzenesulfonate, or $C_1$ to $C_{18}$ alkyl benzenesulfonate.

The present invention also provides a method for making an acid copolymer/quaternary amine antistatic mixture comprising mixing with heat (A) a polymer containing carboxylic acid moieties and (B) an antistatically effective amount of a quaternary amine wherein:
(A) the polymer containing carboxylic acid moieties is a copolymer of (i) a major amount by mol % of an alpha-olefin of the formula $RCH=CH_2$ wherein R is H or $C_3$ to $C_8$ alkyl, and (ii) a minor amount by mol % of an alpha,beta-ethylenically unsaturated carboxylic acid, and
(B) the quaternary amine is of the formula $[(R^1)(R^2)(R^3)(R^4)N]^+[X]^-$ wherein $R^1$ is selected from H, aryl, or $C_1$ to $C_{50}$ alkyl optionally having one or more non-contiguous C=O or NHC=O or —S— or —O— in the carbon chain, or the same as $R^2$;

each of $R^2$, $R^3$ and $R^4$ is the same or different and selected from H, $C_1$ to $C_{18}$ alkyl optionally substituted with one or more OH or from —($R^5$—O)$_a$—H where a is an integer from 1 to 10 and $R^5$ is ethylene or propylene; and X is an anion selected from chloride, bromide, iodide, fluoride, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, citrate, trifluoroacetate, propionate, tartrate or carbonate.

The present invention also provides a method for making an antistatic film comprising (1) mixing with heat (A) a polymer containing carboxylic acid moieties and (B) an antistatically effective amount of a quaternary amine wherein:

(A) the polymer containing carboxylic acid moieties is a copolymer of (i) a major amount by mol % of an alpha-olefin of the formula RCH=CH$_2$ wherein R is H or $C_1$ to $C_8$ alkyl, and (ii) a minor amount by mol % of an alpha,beta-ethylenically unsaturated carboxylic acid, and (B) the quaternary amine is of the formula $[(R^1)(R^2)(R^3)(R^4)N]^+[X]^-$ $R^1$ is selected from H, aryl, or $C_1$ to $C_{50}$ alkyl optionally having one or more non-contiguous C=O or NHC=O or —S— or —O— in the carbon chain, or the same as $R^2$;

each of $R^2$, $R^3$, and $R^4$ is the same or different and selected from H, $C_1$ to $C_{18}$ alkyl optionally substituted with one or more OH or from —($R^5$—O)$_a$—H where a is an integer from 1 to 10 and $R^5$ is ethylene or propylene; and X is an anion selected from chloride, bromide, iodide, fluoride, nitrate, fluoborate, phosphate, sulfate, $C_1$ to $C_8$ alkyl sulfate, formate, $C_1$ to $C_8$ alkyl or $C_6$ to $C_{24}$ alkaryl or aryl sulfonate, acetate, citrate, trifluoroacetate, propionate, tartrate or carbonate; and (2) forming the resultant into a film having one or more layers.

The present invention also provides a permanently antistatic film resultant from mixing with heat and forming into a film having one or more layers (A) a polymer containing carboxylic acid moieties and (B) an antistatically effective amount of a quaternary amine wherein:

(A) the polymer containing carboxylic acid moieties is a copolymer of (i) a major amount by mol % of an alpha-olefin of the formula RCH=CH$_2$ wherein R is H or $C_1$ to $C_8$ alkyl, and (ii) a minor amount by mol % of an alpha,beta-ethylenically unsaturated carboxylic acid, and (B) the quaternary amine is of the formula $[(R^1)(R^2)(R^3)(R^4)N]^+[X]^-$ wherein $R^1$ is selected from H, aryl, or $C_1$ to $C_{50}$ alkyl optionally having one or more non-contiguous C=O or NHC=O or —S— or —O— in the carbon chain, or the same as $R^2$;

each of $R^2$, $R^3$, and $R^4$ is the same or different and selected from H, $C_1$ to $C_{18}$ alkyl optionally substituted with one or more OH or from —($R^5$—O)$_a$—H where a is an integer from 1 to 10 and $R^5$ is ethylene or propylene; and X is an anion selected from chloride, bromide, iodide, fluoride, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, citrate, trifluoroacetate, propionate, tartrate, or carbonate.

The present invention also provides a permanently antistatic film comprising a film obtained from mixing with heat and forming into a film (A) ethylene-acrylic acid or ethylene-methacrylic acid and (B) a quaternary amine of the formula $[R^1R^2R^3R^4N]^+[X]^-$ where $R^1$ is a $C_4$ to $C_{30}$ straight or branched alkyl optionally including one or more ether linkages, each of $R^2$ and $R^3$ and $R^4$ is the same or different and selected from methyl or ethyl, and X is chloride, methyl sulfate, or ethyl sulfate.

The present invention also provides a film comprising a 5-layer, permanently antistatic film having the layers in direct surface-to-surface contact with each other in the following order:

(1) a first layer, said layer being an outside layer comprising about 90% or more by weight of ethylene vinyl acetate copolymer and about 10% or less by weight of antiblock, (2) a second layer, said layer being an interior layer comprising about 65% or more by weight ethylene vinyl acetate copolymer, and about 35% or less by weight of a mixture of (A) a polymer containing carboxylic acid moieties and (B) an antistatically effective amount of a quaternary amine wherein:

(A) the polymer containing carboxylic acid moieties is a copolymer of (i) a major amount by mol % of an alpha-olefin of the formula RCH=CH$_2$ wherein R is H or $C_1$ to $C_8$ alkyl, and (ii) a minor amount by mol % of an alpha,beta-ethylenically unsaturated carboxylic acid, and (B) the quaternary amine is of the formula $[(R^1)(R^2)(R^3)(R^4)N]^+[X]^-$ wherein $R^1$ is selected from H, aryl, or $C_1$ to $C_{50}$ alkyl optionally having one or more non-contiguous C=O or NHC=O or —S— or —O— in the carbon chain, or the same as $R^2$;

each of $R^2$, $R^3$, and $R^4$ is the same or different and selected from H, $C_1$ to $C_{18}$ alkyl optionally substituted with one or more OH or from —($R^5$—O)$_a$—H where a is an integer from 1 to 10 and $R^5$ is ethylene or propylene; and X is an anion selected from chloride, bromide, iodide, fluoride, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, citrate, trifluoroacetate, propionate, tartrate, or carbonate, (3) a third layer, said layer being a core layer comprising about 65% or more by weight of a mixture of linear low density polyethylene copolymer and ethylene vinyl acetate copolymer and about 35% or less by weight of a mixture of (A) a polymer containing carboxylic acid moieties and (B) an antistatically effective amount of a quaternary amine wherein:

(A) the polymer containing carboxylic acid moieties is a copolymer of (i) a major amount by mol % of an alpha-olefin of the formula $RCH=CH_2$ wherein R is H or $C_1$ to $C_8$ alkyl, and (ii) a minor amount by mol % of an alpha,beta-ethylenically unsaturated carboxylic acid, and (B) the quaternary amine is of the formula

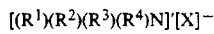

wherein $R^1$ is selected from H, aryl, or $C_1$ to $C_{50}$ alkyl optionally having one or more non-contiguous $C=O$ or $NHC=O$ or $-S-$ or $-O-$ in the carbon chain, or the same as $R^2$;

each of $R^2$, $R^3$, and $R^4$ is the same or different and selected from H, $C_1$ to $C_{18}$ alkyl optionally substituted with one or more OH or from $-(R^5-O)_a-H$ where a is an integer from 1 to 10 and $R^5$ is ethylene or propylene; and X is an anion selected from chloride, bromide, fluoride, iodide, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, citrate, trifluoroacetate, propionate, tartrate, or carbonate.

(4) a fourth layer, comprising an interior layer the same as layer (2), and (5) a fifth layer, comprising an outside layer the same as layer (1).

DETAILED DESCRIPTION OF THE INVENTION

The acid copolymer is a polymer containing carboxylic acid moieties. By "polymers containing carboxylic acid moieties" as that term is used herein it is intended to mean copolymers of (i) a major amount by mol % of an alpha-olefin having the formula $RCH=CH_2$ wherein R is H or $C_1$ to $C_8$ alkyl and (ii) a minor amount by mol % of an alpha,beta-ethylenically unsaturated carboxylic acid. Preferably, the alpha,beta-ethylenically unsaturated carboxylic acid is present in an amount by mol % of about 40% or less, more preferably about 30% or less, most preferably about 20% or less. Also, by the term "polymers containing carboxylic acid moieties", it is intended to mean that the copolymer of an alpha-olefin having the formula $RHC=CH_2$ wherein R is H or $C_1$ to $C_8$ alkyl and an alpha,beta-ethylenically unsaturated carboxylic acid may be wholly or partially neutralized with a suitable cation such as zinc cation or sodium cation. Thus, the polymer containing carboxylic acid moieties may be an ionomer.

The acid copolymer need not necessarily comprise a two component polymer. Thus, although the olefin content of the acid copolymer preferably is at least 50 mol percent, more than one olefin may be employed. Also, other copolymerizable monoethylenically unsaturated monomers may be employed in combination with the olefin and the carboxylic acid comonomer. It is intended also to include terpolymers. Accordingly, acid copolymers or terpolymers suitable for use in the present invention include, but are not limited to, ethylene/acrylic acid copolymers, ethylene/methacrylic acid copolymers, ethylene/itaconic acid copolymers, ethylene/methyl hydrogen maleate copolymers, ethylene/maleic acid copolymers, ethylene/methyl hydrogen maleate/ethyl acrylate terpolymers, ethylene/methacrylic acid/vinyl acetate terpolymers, ethylene/acrylic acid/vinyl acetate terpolymers, ethylene/acrylic acid/vinyl alcohol terpolymers, ethylene/propylene/acrylic acid terpolymers, ethylene/styrene/acrylic acid terpolymers, ethylene/acrylic acid/methyl methacrylate terpolymers, ethylene/methacrylic acid/ethyl acrylate terpolymers, ethylene/itaconic acid/methyl methacrylate terpolymers, ethylene/methacrylic acid/acrylonitrile terpolymers, ethylene/fumaric acid/vinyl methyl ether terpolymers, ethylene/vinyl chloride/acrylic acid terpolymers, ethylene/vinylidene chloride/acrylic acid terpolymers, ethylene/vinyl flouride/methacrylic acid terpolymers, and ethylene/chlorotrifluroethylene/methacrylic acid terpolymers.

The copolymer of an alpha-olefin having the formula $RCH=CH_2$ wherein R is H or $C_1$ to $C_8$ alkyl and an alpha,beta-ethylenically unsaturated carboxylic acid representatively may be produced by the free radical copolymerization of ethylene and a carboxylic acid comonomer therefor such as acrylic acid or methacrylic acid. Suitable such acid copolymers are the Primacor (TM) polymers, supplied by Dow Chemical Company, Midland, Mich. Primacor is produced by the copolymerization of ethylene and acrylic acid. Ethylene-acrylic acid copolymers are herein referred to as EAA copolymer. A very suitable Primacor polymer is Primacor 1410 or Primacor 5981. Other suitable such acid copolymers are sold under the trade-name Nucrel by du Pont; they are produced by the copolymerization of ethylene and methacrylic acid. Ethylene-methacrylic acid copolymers are herein referred to as EMAA copolymers. Ionomers are commercially available as Surlyn (R) from the E. I. du Pont de Nemours Company of Wilmington, Del., and are described in detail in U.S. Pat. Nos. 3,355,319 and 3,845,163.

The amine is a quaternary amine of the formula

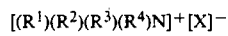

wherein $R^1$ is selected from H, aryl, or $C_1$ to $C_{50}$ alkyl optionally having one or more non-contigous $C=O$ or $NHC=O$ or $-S-$ or $-O-$ in the carbon chain, or the same as $R^2$;

each of $R^2$, $R^3$, and $R^4$ is the same or different and selected from H, $C_1$ to $C_{18}$ alkyl optionally substituted with one or more OH or from $-(R^5-O)_a-H$ where a is an integer from 1 to 10 and $R^5$ is ethylene or propylene; and X is an anion selected from chloride, bromide, iodide, fluoride, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, citrate, propionate, tartrate or carbonate. Preferably, the $C_1$ to $C_8$ alkyl phosphate is methyl phosphate or ethyl phosphate, the $C_1$ to $C_8$ alkyl sulfate is methyl sulfate or ethyl sulfate, and the $C_1$ to $C_8$ alkyl or $C_6$ to $C_{24}$ alkaryl or aryl sulfonate is methanesulfonate, butanesulfonate, benzenesulfonate, or $C_1$ to $C_{18}$ alkyl benzenesulfonate.

By "quaternary amine" as that term is employed herein, it is intended to include quaternary ammonium compounds and/or quaternary ammonium salts.

Suitable quaternary amines (QA) may be chosen from, but are not limited to, the methyl chloride salts of ethoxylated fatty amines. Commercial ones are available from the Tomah Division (Milton, Wis.) of Exxon Chemical and are represented by the formula:

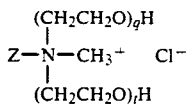

where Z is an alkyl or alkoxy radical, and q+t is the total number of moles of ethylene oxide in the chains. Examples of commercially available ones are as follows:

COMMERCIAL QUATERNARY AMINES

| QA Product Indentification Number | Z | q + t |
| --- | --- | --- |
| Q-14-2 | $C_{10}OC_3$ | 2 |
| Q-14-5 | $C_{10}OC_3$ | 5 |
| Q-14-15 | $C_{10}OC_3$ | 15 |
| Q-17-2 | $C_{13}OC_3$ | 2 |
| Q-S-2 | Soya | 2 |
| Q-S-5 | Soya | 5 |
| Q-S-15 | Soya | 15 |
| Q-18-2 | $C_{18}$ | 2 |
| Q-18-5 | $C_{18}$ | 5 |
| Q-18-8 | $C_{18}$ | 8 |
| Q-18-10 | $C_{18}$ | 10 |
| Q-18-15 | $C_{18}$ | 15 |
| Q-T-2 | Tallow | 2 |
| Q-T-5 | Tallow | 5 |
| Q-T-15 | Tallow | 15 |
| Q-DT-3 | "Tallow Diamine" | 3 |

Other very suitable quaternary amines are the ethyl sulfate salts or methyl sulfate salts of alkoxylated fatty amines. Commercial ones are available under the tradename Emerstat 6660 from Emery Industries and it is believed from applicants' own chemical analysis that they are represented by the formula: $(A)(A')N[(CH_2CH_2O)_nH]_2^+ A'OSO_3^-$ where A is $C_8$ to $C_{20}$ alkyl, A' is ethyl and n is an integer from 1 to 4. Also suitable are methyl sulfate salts such as that sold under the tradename Cyastat by Cyanamid; it has the formula $C_{11}H_{23}CONHC_3H_6N(CH_3)_3^+CH_3OSO_3^-$. Also suitable are ethosulfate salts such as that sold under the trade-name Larostat 264A Anhydrous, which is a modified soyadimethyl ethylammonium ethosulfate.

Additional QA's may be prepared by reacting a tertiary amine (TA) and an acid or alkylating agent, as further described in the Examples below.

The polymer containing carboxylic acid moieties and the quaternary amine are combined by mixing with heat. Optionally, a polymer compatible therewith, such as a polyolefin, may be blended in the mixture. Any suitable mixing means may be employed such as a blender or a twin screw extruder. The heat should be from about 50° C. to 290° C., more preferably about 100° C. to 250° C., even more preferably about 100° C. to 200° C. Then the resultant may be formed into a film such as by heat pressing on a platen or by any of the various methods further discussed below. The film is permanently antistatic. It will dissipate an applied charge of ±5000 Vdc in less than about 3000 ms, more preferably less than 2000 ms, using the method described in Federal Test Method Standard 101c, Method 4046.1, even after a 24 hour water shower. This is unlike prior polymeric films containing an antistatic agent to give them antistatic characteristics, which characteristics can be washed out after a 24 hour water shower because the agents operate by migrating to the surface and attracting moisture. Furthermore, in some embodiments, the films survive 1 day, more preferably 3 days, even more preferably 5 days, and most preferably 12 days in a hot oven at approximately 70° C. and still exhibit this static decay time of less than about 3000 ms, more preferably less than about 2000 ms. Based on the % weight amount of polymer containing carboxylic acid moieties, it is preferred that the quaternary amine be present in a weight % amount up to about 50%, more preferably up to about 30%, even more preferably up to about 20%. Based on the total composition weight, which optionally may contain polyolefin, preferably the quaternary amine is present in a weight % amount of about 0.001% to about 30%, more preferably about 0.01% to about 20%, and even more preferably about 2% to about 10%.

It is also noted that in multi-layer film embodiments, the layer or layers comprising the composition of quaternary amine and acid copolymer should comprise about half the thickness or more of the multilayer film for the film to be permanently antistatic, i.e. exhibit an SDT under 3000 ms after a 24-hour water shower. Otherwise, the film as is, will exhibit an SDT under 3000 ms, but after the 24-hour water shower the film will not accept a charge. It is also further preferred that both skin layers of the multi-layer film comprise the composition of quaternary amine and acid copolymer, as compared to 1 skin layer or a core layer, for the film to have a permanent antistatic surface resistivity, i.e. a surface resistivity from $10^5$ to $10^{12}$ ohms/square after a 24-hour water shower. All of this is illustrated by Example XII below wherein the multilayer film had only 1/5 its thickness (i.e. 1 layer out of 5) be the composition of quaternary amine and acid copolymer. This film exhibited an antistatic SDT of 1824 ms and 1852 ms when tested as is, but would not accept a charge after a 24-hour water shower. Also this film exhibited an antistatic surface resistivity of $5.9 \times 10^{11}$ ohms/square when tested as is, but showed an insulative surface resistivity of $1.9 \times 10^{14}$ ohms/square after a 24-hour water shower.

Many polymer resins are suitable polymers for blending with the new, acid copolymer/quaternary amine. Unless specifically set forth and defined or otherwise limited, the terms "polymer" or "polymer resin" as used herein generally include, but are not limited to, homopolymers, copolymers, such as, for example block, graft, random and alternating copolymers, terpolymers etc. and blends and modifications thereof. Furthermore, unless otherwise specifically limited the terms "polymers" or "polymer resin" shall include all possible structures of the material. These structures include, but are not limited to, isotactic, syndiotactic and random symmetries. Particularly suitable for blending are the polyolefins. The term "polyolefin" as used herein generally includes, but is not limited to, materials such as polyethylene (PE), polypropylene (PP), ethylene-vinyl acetate (EVA) and the like, the homopolymers, copolymers, terpolymers etc. thereof, and blends and modifications thereof. The term "polyolefin" shall include all possible structures thereof, which includes, but is not limited to, isotactic, syndiotactic and random symmetries.

According to Modern Plastics Encyclopedia, 1985-86, polyethylenes having densities ranging from about 0.900 g/cc to about 0.935 g/cc are called low density polyethylenes (LDPE), while those having densities from about 0.936 g/cc to about 0.940 g/cc are called medium density polyethylenes (MDPE), and those having densities from about 0.941 g/cc to about 0.965 g/cc and over are called high density polyethylenes (HDPE). The older, classic low density types of polyethylenes are usually polymerized at high pressures and temperatures whereas, the older, classic high density types are usually polymerized at relatively low temperatures and pressures. The term "linear low density polyethylene" (LLDPE) as used herein, for a type of polyolefin, refers to the newer copolymers of a major amount of ethylene with a minor amount of one or more comonomers selected from $C_3$ to $C_{10}$ alpha olefins such as butene-1, pentene-1, hexene-1, 4-methyl-pentene-1, octene-1, etc. in which the molecules thereof comprise long chains with few side chains or branched structures achieved by low pressure polymerization. LLDPE has a density preferably in the range from about 0.911 g/cc to about 0.935 g/cc, and more preferably in the range of from about 0.912 g/cc to about 0.928 g/cc. Also, very low density linear low density polyethylenes (VLDPE) may be employed, and such have a density from about 0.910 g/cc to about 0.860 g/cc, or even lower.

The term "ethylene vinyl acetate copolymer" (EVA) as used herein, for a type of polyolefin refers to a copolymer formed from ethylene and vinyl acetate (VA) monomers. The ethylene derived units in the copolymer are present in major amounts by weight and the VA derived units in the copolymer are present in minor amounts by weight. For film making purposes, it is preferred that the VA content of the EVA be from about 3% to about 25%.

The term "polypropylene" (PP) as used herein for a type of polyolefin refers to polymers of propylene, and includes homopolymers, copolymers, such as for example block, graft, random, and alternating, copolymers, terpolymers etc. and blends and modifications thereof.

The term "ethylene/alkyl-acrylate copolymer" (EA-1Acr) as used herein refers to a copolymer formed from ethylene and alkyl acrylate wherein the alkyl moiety has 1 to 8 carbon atoms and the ethylene derived units in the copolymer are present in major amounts by weight and the alkylacrylate derived units in the copolymer are present in minor amounts by weight. Thus, the term "ethylene/methyl acrylate copolymer" (EMA) as used herein refers to a copolymer formed from ethylene and methyl acrylate monomers. The term "ethylene/ethyl acrylate copolymer" (EEA) as used herein refers to a copolymer formed from ethylene and ethyl acrylate monomers. The term "ethylene/butyl acrylate copolymer" (EBA) as used herein refers to a copolymer formed from ethylene and butyl acrylate monomers. Many suitable EBA's are commercially available and these have a butyl acrylate content from about 3% up to about 18% by weight. USI is a commercial supplier of Resin No. 4895, which is an EBA having about 3% by weight butyl acrylate and a melt index of about 3 and a melting point of about 106° to 110° C.

Blends of all families of polyolefins, such as blends of EVA, EA1Acr, PP, LDPE, HDPE, VLDPE, and LLDPE, may also be advantageously employed.

Measuring the antistatic property: The antistatic property is exhibited by the ability of the polymer containing the agent to promote static charge decay, i.e. to dissipate a static charge. The polymer alone will not dissipate a static charge, but the polymer containing the agent is able to dissipate 99% of an applied static charge of ±5000 volts direct current (Vdc) in a short amount of time, i.e. less than 3 seconds, more preferably less than 2 seconds (2000 milliseconds). Federal Test Method Standard 101c, Method 4046.1, "Electrostatic Properties of Materials" states less than 2000 ms and thus it is preferred to have a material that complies with 101c. Decay meters for measuring the time for dissipation of the applied volts are commercially available, such as the 406c static decay meter supplied by Electrotech Systems, Inc. Unless otherwise indicated in the Examples below, the films, prior to testing, were equilibrated at less than about 15% relative humidity (RH) at about room temperature (RT) for about 24 hours.

Some films were tested for triboelectric charge generation. Two aluminum plates were used for this test. Plate 1 was a ground plane and was about 12 inches (30.5 cm)×12 inches (30.5 cm)×3/16 inch (0.5 cm) in size. Plate 2 was about 4 inches (10.2 cm)×3 inches (7.6 cm)×3/16 inch (0.5 cm) in size and had a non-contacting static voltmeter attached to it. Plate 2 also had an insulating rod or handle attached to it to allow the person performing the test to separate the plates without touching them and affecting the charge accumulation. The material under test was placed on Plate 1. Plate 2 was pushed against the material to make intimate contact with the sample. Plate 2 was then separated rapidly up against a stop, while the sample remained in contact with Plate 1. This stop limited the travel to approximately 1 inch (2.54 cm) of separation between the two plates. This procedure was repeated 4 times and the voltmeter readings averaged. The principle of this measurement is that when two materials are placed in contact and then separated they give up or take on electrons thus leaving both materials with a net charge. Since one of the materials in the test is a metal plate, the charge on it can be measured by a static voltmeter. The magnitude and polarity of the charge is then an indicator of the tribo-charging propensity of the material under test. A desirable reading is between about −200 volts and +200 volts.

Some of the films were tested for surface resistivity and volume resistivity according to ASTM D257. There is not necessarily a correlation between the surface or volume resistivity of a film and the ability of a film to decay or dissipate charges. Thus, the term "antistatic" as used herein describes a material which can dissipate 99% of an applied static charge of ±5000 Vdc in a short amount of time, preferably a static decay time less than about 3 seconds, more preferably less than about 2 seconds (Federal Test Method Standard 101c, Method 4046.1, "Electrostatic Properties of Materials"). If the material also happens to have an antistatic resistivity, i.e. a surface resistivity of about $10^5$ to $10^{12}$ ohms/square as further described below, then that material will be described using the term "antistatic surface resistivity."

The Department of Defense and the Electronics Industry Association have standards on surface resistivity of a material in ohms/square as follows:

| Surface Resistivity Ranges (ohms/square) | | |
|---|---|---|
| Insulative | Antistatic or Static Dissipative | Conductive |
| greater than $10^{12}$ | $10^{12}$ to $10^5$ | less than $10^5$ |

It is noted that some of the 5-layer films of the invention, as illustrated by Examples XIII and XIV below, have both a preferred static decay time of about 3000 milliseconds or less and a static dissipative (as opposed to insulative) surface resistivity of $10^{12}$ to $10^5$ ohms/square, even after a 24-hour water shower or after 12 days in a hot oven. Thus these 5-layer films are permanently antistatic by the definition of static decay time and permanently antistatic by the definition of antistatic surface resistivity; neither the 24-hour water shower nor the 12-day hot oven takes out the "antistatic" characteristic.

Some of the films were tested for crazing, i.e. polycarbonate compatability, which was a test developed by General Electric Company, published as their "LEXAN (®) Resin Technifacts" T-47 test method. This test consists of bending or flexing test coupons or bars of LEXAN (®) about 1/8 inch (0.32 cm) thick on metal jigs to several known stress levels of about 500 to 3400 psi (35 to 239 kg/cm$^2$) and the material being evaluated is then applied to the stressed coupons and the combination maintained at several temperatures for 5 days. The temperatures are about 73° F. (22.8° C.), 120° F. (48.9° C.), 158° F. (70° C.), and 185° F. (85° C.). A comparison of the strain independent of the material being evaluated, the radius of the curvature of the upper surface of the jig, and the stress level of the LEXAN (®) bars is as follows:

| STRESS LEVEL ⅛" THICK BARS UNFILLED LEXAN RESIN | | RADIUS OF UPPER SURFACE OF JIG | | STRAIN INDEPENDENT OF MATERIAL |
|---|---|---|---|---|
| PSI | kg/cm$^2$ | Inches | cm | percent |
| 500 | 35 | 42.437 | 107.8 | 0.15 |
| 750 | 53 | 28.270 | 71.8 | 0.22 |
| 1000 | 70 | 21.187 | 53.8 | 0.29 |
| 1250 | 88 | 17.063 | 43.3 | 0.37 |
| 1500 | 105 | 14.103 | 35.8 | 0.44 |
| 1750 | 123 | 12.080 | 30.7 | 0.51 |
| 2000 | 141 | 10.563 | 26.8 | 0.59 |
| 2250 | 158 | 9.381 | 23.8 | 0.66 |
| 2500 | 176 | 8.437 | 21.4 | 0.74 |
| 2750 | 193 | 7.664 | 19.5 | 0.81 |
| 3000 | 211 | 7.020 | 17.8 | 0.88 |
| 3400 | 239 | 6.187 | 15.7 | 1 |

At the end of the exposure, the bars are visually checked for crazing. Results are reported as the maximum stress to which the bar can be subjected while in contact with the particular environment without the occurrence of crazing. It is desired that the film exhibit no crazing or only very slight crazing at a temperature 158° F. (70° C.) and stress of 1700 psi, more preferably a temperature of 185° F. (85° C.) and stress of 1700 psi.

Manufacture of Films: Typically, in the manufacture of films, a suitable polymer usually in the form of pellets or the like, is brought into a heated area where the polymer feed is melted and heated to its extrusion temperature and extruded as a tubular "blown bubble" through an annular die. Other methods, such as "slot die" extrusion wherein the resultant extrudate is in planar, as opposed to tubular, form are also well known. If heat shrinkable film is desired, then after extrusion, the film is typically cooled and then reheated and stretched, i.e. oriented by "tenter framing" or by inflating with a "trapped bubble", to impart the heat-shrinkable property to the film, as is further described below. If desired, high energy irradiation, typically via an electron beam, preferably takes place prior to the stretching for orienting the film. However, for the present invention, such irradiation is not necessary since a very suitable packaging film having permanent antistatic characteristics is obtained without irradiation. Below, first is described the general process for making and orienting film. Then irradiation is described.

More particularly, manufacturing of films may be accomplished as follows. For instance, the manufacture of shrink films may be generally accomplished by extrusion (single layer films) or coextrusion (multilayer films) of thermoplastic resinous materials which have been heated to or above their flow or melting point from an extrusion or coextrusion die in, for example, either tubular or planar (sheet) form, followed by a post extrusion cooling. The stretching for orientation may be conducted at some point during the cool down and while the film is still hot and within its orientation temperature range followed by completing the cooling. Alternatively, after the post extrusion cooling, the relatively thick "tape" extrudate is then reheated to a temperature within its orientation temperature range and stretched to orient or align the crystallites and/or molecules of the material and then cooled. The orientation temperature range for a given material or materials will vary with the different resinous polymers and/or blends thereof which comprise the material. However, the orientation temperature range for a given thermoplastic material may generally be stated to be below the crystalline melting point of the material but above the second order transition temperature (sometimes referred to as the glass transition point) thereof. Within this temperature range, the material may be effectively oriented. The terms "orientation" or "oriented" are used herein to describe generally the process steps and resultant product characteristics obtained by stretching and immediately cooling a resinous thermoplastic polymeric material which has been heated to a temperature within its orientation temperature range so as to revise the intermolecular configuration of the material by physical alignment of the crystallites and/or molecules of the material to improve certain mechanical properties of the film such as, for example, shrink tension and orientation release stress. Both of these properties may be measured in accordance with ASTM D 2838-81. When the stretching force is applied in one direction monoaxial orientation results. When the stretching force is simultaneously applied in two directions biaxial orientation results. The term oriented is also herein used interchangeably with the term "heat-shrinkable" with these terms designating a material which has been stretched and set by cooling while substantially retaining its stretched dimensions. An oriented (i.e. heat-shrinkable) material will tend to return to its original unstretched (unextended) dimensions when heated to an appropriate elevated temperature.

An "oriented" or "heat-shrinkable" material is defined herein as a material which, when heated to an appropriate temperature above room temperature (for example 96° C.), will have a free shrink of about 5% or greater in at least one linear direction.

Returning to the basic process for manufacturing the film as discussed above, it can be seen that the film, once extruded (or coextruded if it is a multi-layer film) and initially cooled, is then reheated to within its orientation temperature range and oriented by stretching. The stretching to orient may be accomplished in many ways such as, for example, by "trapped bubble" techniques or "tenter framing". These processes are well known to those in the art and refer to orientation procedures whereby the material is stretched in the cross or transverse direction (TD) and/or in the longitudinal or machine direction (LD or MD). After being stretched, the film is quickly cooled while substantially retaining its stretched dimensions to cool the film rapidly and thus set or lock-in the oriented molecular configuration.

Of course, if a film having little or no orientation is desired, e.g. non-oriented or non-heat shrinkable film, the film may be formed from a non-orientable material or, if formed from an orientable material may be formed from a tube by using a "trapped bubble" technique commonly known as the "hot blown" technique. In forming a hot blown film, the tube is not cooled initially after extrusion or coextrusion but rather is first stretched by a hot blown bubble essentially immediately after extrusion while the tube is still at an elevated temperature above the orientation temperature range of the material. Thereafter, the film is cooled, by well-known methods. Those of skill in the art are well familiar with this process and the fact that the resulting film has substantially unoriented characteristics. Other methods for forming unoriented films are well known. Exemplary, is the method of cast extrusion or cast coextrusion which, likewise, is well known to those in the art.

Whichever film has been made (the non-oriented molecular configuration or the stretch-oriented "heat-shrinkable" molecular configuration), it may then be stored in rolls and utilized to package a wide variety of items. If the material was manufactured by "trapped bubble" techniques the material may still be in tubular form or it may have been slit and opened up to form a sheet of film material. In this regard, the product to be packaged may first be enclosed in the material by heat sealing the film to itself where necessary and appropriate to form a pouch or bag and then inserting the product therein. Alternatively, a sheet of the material may be utilized to overwrap the product, or the product may be vacuum skin packaged with the material. These packaging methods are all well known to those of skill in the art.

If the material is of the heat-shrinkable, i.e. "oriented", type, then after wrapping, the enclosed product may be subjected to elevated temperatures, for example, by passing the enclosed product through a hot air tunnel. This causes the enclosing heat shrinkable film to shrink around the product to produce a tight wrapping that closely conforms to the contour of the product. As stated above, the film sheet or tube may be formed into bags or pouches and thereafter utilized to package a product. In this case, if the film has been formed as a tube it may be preferable first to slit the tubular film to form a film sheet and thereafter form the sheet into bags or pouches. Such bag or pouch forming methods, likewise, are well known to those of skill in the art.

Alternative methods of producing films of this type are known to those in the art. One well-known alternative is the method of forming a multi-layer film by an extrusion coating rather than by an extrusion or coextrusion process as was discussed above. In extrusion coating a first tubular layer is extruded and thereafter an additional layer or layers is simultaneously or sequentially coated onto the outer surface of the first tubular layer or a successive layer.

The above general outline for manufacturing of films is not meant to be all inclusive since such processes are well known to those in the art. For example, see U.S. Pat. Nos. 4,274,900; 4,229,241; 4,194,039; 4,188,443; 4,048,428; 3,555,604; 3,741,253; 3,821,182 and 3,022,543. The disclosures of these patents are generally representative of such processes and are hereby incorporated by reference.

Many other process variations for forming films are well known to those in the art. For, example, conventional pressing, thermoforming or laminating techniques (including corona laminating) may be employed. For instance, multiple layers may be first coextruded with additional layers thereafter being laminated thereon, or two multi-layer tubes may be coextruded with one of the tubes thereafter being laminated onto the other.

If a heat shrinkable, i.e. "oriented", film is desired, after extrusion and cooling, then after irradiation (or without irradiation), the tube may then be heated to soften it, and then the softened tube is passed through pinch rolls and stretch oriented by the trapped blown bubble technique discussed above.

Irradiation, if desired, may be accomplished by the use of high energy electrons, ultra violet radiation, X-rays, gamma rays, beta particles etc. Preferably, electrons are employed up to about 20 megarads (Mr) dosage level. The irradiation source can be any electron beam generator operating in a range of about 150 kilovolts to about 6 megavolts with a power output capable of supplying the desired dosage. The voltage can be adjusted to appropriate levels which may be for example 1,000,000 or 2,000,000 or 3,000,000 or 6,000,000 or higher or lower. Many apparatus for irradiating films are known to those of skill in the art. The irradiation is usually carried out at a dosage between about 1 Mr (10 kilogrey) and about 20 Mr (200 kilogrey), with a preferred dosage range of about 2 Mr (20 kilogrey) to about 12 Mr (120 kilogrey). Irradiation can be carried out conveniently at room temperature, although higher and lower temperatures, for example, 0° C. to 60° C. may be employed.

It is also generally well known in the art that irradiation, such as by electron beam irradiation, of certain polymeric film materials generally results in a material having improved heat shrink properties, abuse resistance, structural integrity, tensile strength, puncture resistance, and/or delamination resistance. Such physical toughness improvements from irradiation, are discussed in U.S. Pat. No. 3,022,543 (1962) to Baird et al, U.S. Pat. No. 4,178,401 (1979) to Weinberg and U.S. Pat. No. 3,741,253 to Brax et al.

Advantageously, an outside polymeric layer of a film may include a small amount of about 10% by weight or less, more desirably about 7% by weight or less of an antiblock, to help alleviate any tackiness. A suitable antiblock is EPE 8160 supplied by Teknor Apex.

The following Examples are intended to illustrate the preferred embodiments of the invention and comparisons thereto. It is not intended to limit the invention thereby.

Unless indicated otherwise in the Examples, the testing for static decay time (SDT) was done after equilibration for 24 hours, at about room temperature (RT), at less than about 15% relative humidity (RH). Also it is noted that sometimes SDT testing was done to samples that had been subjected to abuse such as 1 to 12 days in a hot, about 160° F. (71° C.), oven or a 24-hour water shower. Where the oven is designated as "humid", a beaker of water had been kept in the oven with the film sample during testing to maintain a "humid" atmosphere; otherwise the oven was simply a "dry" or "ambient" oven, without any water beaker.

| MATERIALS EMPLOYED IN THE EXAMPLES | | | | |
|---|---|---|---|---|
| ANTIBLOCK | INGREDIENTS | | SUPPLIER | |
| EPE 8160 | Polyethylene Containing Micron Sized Silica | | Teknor Apex | |
| LLDPE | MI* | DENSITY | COMONOMER | SUPPLIER |
| DOWLEX 2045.03 | 1.1 | 0.920 | Octene | Dow Chemical |
| EVA | MI | % VA | COMONOMER | SUPPLIER |
| LD318.92 | 2.0 | 9 | Vinyl Acetate | Exxon |
| EAA | MI | % BY WEIGHT ACRYLIC ACID | % BY WEIGHT ETHYLENE | SUPPLIER |
| PRIMACOR 1410 | 1.5 | 9 | 91 | Dow Chemical |
| PRIMACOR 5981 | 300 | 20 | 80 | Dow Chemical |

| ZINC METHACRYLATE IONOMER OF EMAA | FORMULA | SUPPLIER |
|---|---|---|
| Surlyn 1650 | Partially zinc neutralized ethylene methacrylic acid copolymer | du Pont |

| QA | FORMULA | SUPPLIER |
|---|---|---|
| Q-14-2 | $[C_{10}H_{21}OC_3H_6N(C_2H_4OH)_2CH_3]^+Cl^-$ | Tomah Div. of Exxon |
| Emerstat 6660 | $[H(CH_2)_{8-20}](C_2H_5)N[(C_2H_4O)_{1-4}H]_2^+ C_2H_5OSO_3^-$ | Emery Industries |
| Cyastat | $C_{11}H_{23}CONHC_3H_6N(CH_3)_3^+ CH_3OSO_3^-$ | Cyanamid |
| Larostat 264A Anhydrous | Modified soyadimethyl ethylammonium ethosulfate | Jordan/PPG/Mazer |

| TA | FORMULA | SUPPLIER |
|---|---|---|
| Empigen AB | Lauryl dimethylamine | Albright & Wilson |
| Empigen AY | $H(CH_2)_{10-18}(OC_2H_4)_nN(CH_3)_2$ | Albright & Wilson |
| E-14-2 | $C_{10}H_{21}OC_3H_6N(C_2H_4OH)_2$ | Tomah Div., Exxon |
| DMCA | N,N-dimethylcocoamine | Akzo Chemie |

| ACID OR ALKYLATING AGENT | FORMULA | SUPPLIER |
|---|---|---|
| MSA | Methanesulfonic Acid | Aldrich |
| DBSA | $H(CH_2)_{12-18}C_6H_4SO_3H$ | Alfa/Morton Thiokol |
| DES | Diethyl Sulfate | Aldrich |

*MI is melt index.

EXAMPLE I

LLDPE and EAA (Primacor 5981) were premixed in parts by weight and then blended therein with heating was a QA in parts by weight. The resultant mix of LLDPE+EAA+QA was then further blended in an amount of 33⅓% by wt. with EAA (Primacor 1410) in an amount of 66⅔% by wt. and that was hot blown into an extruded, tubular film. Films were about 1.5 to 2 mils (0.04 to 0.05 mm) thick. What was made is listed in Table IA.

TABLE IA 60 parts by wt LLDPE [Dowlex2045.03]  
15 parts by wt QA [Q-14-2]       ⎫ 33⅓% by wt mix of LLDPE + EAA + QA  
30 parts by wt EAA [Primacor 5981]   ⎭

66⅔% by wt EAA [Primacor1410]

100% Resultant Film

Then, the following electrical measurements were taken on samples of film as reported in Table IB.

TABLE IB

| SAMPLE | | | |
|---|---|---|---|
| A | Static Decay Time as is | | 180 ms |
| B | Static Decay Time after 24 hours water shower | | 992 ms |
| C | Static Decay Time after days in hot oven at 71° C. | 3 days | 783 ms |
| | | 5 days | 1149 ms |
| | | 9 days | 7340 ms |
| | | 12 days | 14683 ms |
| D | Surface resistivity as is | | $2 \times 10^{10}$ ohms/square |
| E | Volume resistivity as is | | $8.7 \times 10^{10}$ ohm-cm |
| | after 24 hr. water shower | | $1.5 \times 10^{12}$ ohm-cm |
| | after 12 day dry oven | | $1.8 \times 10^{14}$ ohm-cm |

The results show the film performed well as an antistatic film both in terms of static decay time and resistivity, and was resistant to abusive aging, except that it did not survive 12 days in a hot oven with a desirable SDT of about 3000 ms or less.

EXAMPLE II

Films were made as in Example I except that this time the QA was Emerstat 6660 supplied by Emery Industries. The resultant film that was made is as listed in Table IIA below.

TABLE IIA

| 60 parts by wt LLDPE [Dowlex 2045.03]<br>15 parts by wt QA [Emerstat 6660]<br>30 parts by wt EAA [Primacor 5981] | } 33⅓% by wt Mix of LLDPE + EAA + QA |
|---|---|
| | 66⅔% by wt EAA [Primacor 1410] |
| | 100% Resultant Film |

Then, the following electrical measurements were taken on samples of film as reported in Table IIB.

TABLE IIB

| SAMPLE | | | |
|---|---|---|---|
| A | Static Decay Time as is | | 209 ms |
| B | Static Decay Time after 24 hours water shower | | 539 ms |
| C | Static Decay Time after days in hot oven at 71° C. | 3 days | 78 ms |
| | | 5 days | 97 ms |
| | | 9 days | 361 ms |
| | | 12 days | 195 ms |
| D | Surface resistivity as is | | $1.2 \times 10^{11}$ ohms/square |
| E | Volume resistivity as is | | $2.8 \times 10^{12}$ ohm-cm |
| | after 24 hr. water shower | | $2.2 \times 10^{12}$ ohm-cm |
| | after 12 day hot dry oven | | $1.3 \times 10^{12}$ ohm-cm |

The results show the film performed well as an antistatic film both in terms of decay time and resistivity, and was resistant to abusive aging.

EXAMPLE III

By blending with heat using a Berstorff twin screw extruder, a premix of pellets was made. First, 60 parts by weight EVA [LD318.92] and 30 parts by weight EAA [Primacor 5981] were mixed, and then added thereto was 15 parts by wt. QA [Emerstat 6660]. The resultant EVA+EAA+QA was then further blended with more polymer, and hot blown, 5-layer, extruded, tubular film having a thickness of about 4 mil (0.102 mm) was made. The ingredients of each layer were as recited in Table IIIA and are in % by weight.

TABLE IIIA

| OUTSIDE<br>LAYER 1 | INTERIOR<br>LAYER 2 | CORE<br>LAYER 3 | INTERIOR<br>LAYER 4 | OUTSIDE<br>LAYER 5 |
|---|---|---|---|---|
| 95% EVA<br>5% Anti-<br>block | 66⅔% EVA<br>33⅓% Mix of<br>EVA + EAA + QA | 90% LLDPE<br>10% Mix of<br>EVA + EAA + QA | 66⅔% EVA<br>33⅓% Mix of<br>EVA + EAA + QA | 95% EVA<br>5% Anti-<br>block |

Then, the following electrical measurements were taken on samples of film as reported in Table IIIB.

TABLE IIIB

| Abuse<br>Treatment<br>Noted<br>or Film<br>Tested<br>As is | Ohms/square<br>Surface<br>Resistivity | Ohms-cm<br>Volume<br>Resistivity | Static Decay Time(ms) | | Tribo<br>Volts |
|---|---|---|---|---|---|
| | | | 1 Hr.<br>Equilibration<br>for the Film<br>as is or after<br>abuse treatment | 24 Hr.<br>Equilibration<br>for the Film<br>as is or after<br>abuse treatment | |
| As is | $1.8 \times 10^{13}$ | $7.0 \times 10^{13}$ | 111 | 222 | −1.2 |
| 1 Hr. Shower | $1.4 \times 10^{14}$ | $2.1 \times 10^{14}$ | 7 | 177 | 181.9 |
| 3 Hr. Shower | $5.7 \times 10^{14}$ | $1.6 \times 10^{14}$ | Less Than MMSDT* | 115 | 161.5 |
| 24 Hr. Shower | $6.4 \times 10^{12}$ | $4.4 \times 10^{14}$ | Less Than MMSDT | 102 | 76.4 |
| 24 Hr. Hot Humid Oven | $1.6 \times 10^{13}$ | $2.5 \times 10^{14}$ | 183 | 328 | 48.6 |
| Hot Dry Oven | | | | | |
| Day 1 | NT** | NT | 332 | 185 | NT |
| Day 2 | NT | NT | 272 | 178 | NT |
| Day 3 | NT | NT | 180 | 164 | NT |
| Day 4 | NT | NT | 287 | Won't Accept Full Charge | NT |
| Day 5 | NT | NT | 148 | 115 | NT |
| Day 6 | NT | NT | 164 | 348 | NT |
| Day 7 | NT | NT | 359 | 200 | NT |
| Day 8 | NT | NT | NT | 455 | NT |
| Day 9 | NT | NT | 400 | 97 | NT |
| Day 10 | NT | NT | 213 | 259 | NT |
| Day 11 | NT | NT | 247 | 93 | NT |
| Day 12 | $4.2 \times 10^{13}$ | $1.0 \times 10^{16}$ | 299 | 164 | 19.3 |

*MMSDT = minimum measurable static decay time
**NT = not tested

It is noted from Table IIIB that while the resistivity measurements bordered between antistatic and insulative (i.e. $10^{13}$ to $10^{16}$), the static decay times were excellent, well under the preferred 2000 ms or less, even after the hot oven abuse or the water shower abuse. As for the film sample that would not accept a full cahrge after day 4 of the hot dry oven, while it is not intended to be bound to any theory, it is believed this happened due to a mechanical difficulty in that the sample was placed in the test meter in a curved or bowed position instead of a flat, taut position, with respect to the sensing electrode. (It is also noted that 2 similar 5-layer films were made, the only difference being that core layer 3 contained only 5% of the premix of EVA+EAA+QA or contained no premix of EVA+EAA+QA. These similar films performed substantially the same, but for not accepting a full charge during the SDT test after 10 to 12 days in a hot dry oven. While it is not intended to be bound to any theory, it is believed this was also due to a mechanical difficulty in that samples were placed in the test meter in a bowed position.)

EXAMPLE IV

Six tubes of a 5-layer film were made as in Example III, but containing the following amounts of ingredients for each layer as recited in Table IVA below:

TABLE IVA

| Layer 1 | Layer 2 | Layer 3 | Layer 4 | Layer 5 |
| --- | --- | --- | --- | --- |
| 90% EVA | 66⅔% EVA | 90% LLDPE | 66⅔% EVA | 90% EVA |
| 10% Anti-block | 33⅓% Mix of EVA + EAA + QA | 10% Mix of EVA + EAA + QA | 33⅓% Mix of EVA + EAA + QA | 10% Anti-block |

Samples of the 6 tubes of the 5-layer film were tested for static decay time after 1 hour of equilibration and the results were as reported in Table IVB below:

TABLE IVB

| SAMPLE OF FILM | SDT (ms) |
| --- | --- |
| Tube 1 | 14 |
| Tube 2 | 43 |
| Tube 3 | 9 |
| Tube 4 | 23 |
| Tube 5 | 31 |
| Tube 6 | 18 |

As can be seen, excellent SDT's were obtained.

Next 3 sets of 4 samples each of the 6 tubes of 5-layer Film were subjected to a 24-hour water shower. Then, each set was equilibrated for 1 hour, 24 hours, and 48 hours, respectively and then checked for SDT. The results were as reported in Table IVC below:

TABLE IVC

| | | SDT (ms) | | |
| --- | --- | --- | --- | --- |
| Tube | Sample | After 1 Hour Equilibration | After 24 Hours Equilibration | After 48 Hours Equilibration |
| 1 | 1 | Less Than MMSDT* | 24 | 29 |
| 1 | 2 | Less Than MMSDT | 23 | 41 |
| 1 | 3 | Less Than MMSDT | 15 | 23 |
| 1 | 4 | Less Than MMSDT | 16 | 24 |
| 2 | 1 | Less Than MMSDT | 60 | 54 |
| 2 | 2 | Less Than MMSDT | 54 | 50 |
| 2 | 3 | Less Tnan MMSDT | 71 | 66 |
| 2 | 4 | Less Than MMSDT | 70 | 71 |
| 3 | 1 | Less Than MMSDT | 18 | 16 |
| 3 | 2 | Less Than MMSDT | 17 | 20 |
| 3 | 3 | Less Than | 13 | 20 |
| 3 | 4 | Less Than MMSDT | 11 | 18 |
| 4 | 1 | Less Than MMSDT | 76 | 78 |
| 4 | 2 | Less Than MMSDT | 38 | 32 |
| 4 | 3 | Less Than MMSDT | 53 | 60 |
| 4 | 4 | Less Than MMSDT | 84 | 85 |
| 5 | 1 | Less Than MMSDT | 69 | 65 |
| 5 | 2 | Less Than MMSDT | 84 | 76 |
| 5 | 3 | Less Than MMSDT | 32 | 30 |
| 5 | 4 | Less Than MMSDT | 33 | 34 |
| 6 | 1 | Less Than MMSDT | 106 | 108 |
| 6 | 2 | Less Than MMSDT | 114 | 136 |
| 6 | 3 | Less Than MMSDT | 64 | 92 |
| 6 | 4 | Less Than MMSDT | 152 | 161 |

*MMSDT = Minimum measurable static decay time

As can be seen, when film was left to equilibrate for 24 hours, which is as per the specifications of Federal Test Method 101c, then excellent SDT's were obtained. Also, the film retained excellent SDT's even after further equilibration. Thus, these films indeed survived the vigorous abuse of a 24 hour water shower.

EXAMPLE V

For polycarbonate compatability, i.e. crazing tests, also a mono-layer film was extruded from the pellets of premix having the ingredients as recited in Table V-A below:

TABLE V-A 60 parts by wt LLDPE [Dowlex2045.03]
15 parts by wt QA [Q-14-2]
30 parts by wt EAA [Primacor 5981]

and then both a sample from Tube 1 of the 5-layer film of Example IV and a sample from the mono-layer film were tested for crazing of polycarbonate. The results are summarized in Table V-B below:

TABLE V-B

| Test Conditions | | | Tube 1 of | |
| --- | --- | --- | --- | --- |
| | Pressure | | 5-layer | Mono-layer |
| Temperature | PSI | kg/cm² | Film | Film |
| 73° F.(22.8° C.) | 1000 | 70 | N | N |
| | 1700 | 120 | N | N |
| | 2000 | 141 | N | N |
| | 2500 | 176 | N | N |
| | 3400 | 239 | N | N |
| 120° F.(48.9° C.) | 1000 | 70 | N | N |
| | 1700 | 120 | N | N |

TABLE V-B-continued

| Test Conditions | | | Tube 1 of | |
|---|---|---|---|---|
| | Pressure | | 5-layer | Mono-layer |
| Temperature | PSI | kg/cm² | Film | Film |
| | 2000 | 141 | N | N |
| | 2500 | 176 | N | N |
| | 3400 | 239 | VSLC | N |
| 158° F.(70° C.) | 1000 | 70 | N | N |
| | 1700 | 120 | N | N |
| | 2000 | 141 | N | VSLC |
| | 2500 | 176 | N | VSLC |
| | 3400 | 239 | VSLC | VSLC |
| 185° F.(85° C.) | 1000 | 70 | N | N |
| | 1700 | 120 | N | N |
| | 2000 | 141 | N | VSLC |
| | 2500 | 176 | VSLC | VSLC |
| | 3400 | 239 | VSLC | SLC |

N = NO ATTACK
VSLC = VERY SLIGHT CRAZE
SLC = SLIGHTLY CRAZED

As can be seen the 5-layer film D performed excellently and did not exhibit very slight crazing till the most extreme condition of 3400 psi, whereas the monolayer film only showed very slight crazing beginning at a less extreme condition of 2000 psi.

EXAMPLE VI

Quaternary amine additives QA1–QA5 (below) were prepared by mixing the following TA's (tertiary amines) and acids or alkylating agents without solvent for the indicated time/temp.

TABLE VIA

| QA | Formula | TA (gms) | Acid or Alkylating Agent (gms) | Time/Temp. |
|---|---|---|---|---|
| QA1 | $H(CH_2)_{12}N(CH_3)_2H^+$ $CH_3SO_3^-$ | Empigen AB (8.8) | MSA (3.2) | 10 min./ 60° C. |
| QA2 | $H(CH_2)_{12}N(CH_3)_2C_2H_5^+$ $C_2H_5OSO_3^-$ | Empigen AB (8.8) | DES (5.2) | 16 hr./ 60° C. |
| QA3 | $H(CH_2)_{12-18}(OC_2H_4)_n$ $N(CH_3)_2H^+CH_3SO_3$ | Empigen AY (14.4) | MSA (3.2) | 10 min./ 60° C. |
| QA4 | $C_{10}H_{21}OC_3H_6N(C_2H_4OH)_2H^+$ $CH_3SO_3^-$ | E14-2 (12.4) | MSA (3.2) | 10 min./ 60° C. |
| QA5 | $C_{10}H_{21}OC_3H_6N(C_2H_4OH)_2H^+$ $H(CH_2)_{12-18}C_6H_4SO_3^-$ | E14-2 (12.4) | DBSA (10.0) | 10 min./ 60° C. |

Several quaternary amines (QA, 3.6 parts by weight) were blended with Primacor 5981 ethylene-acrylic acid copolymer (7.1 parts by weight) and LD318.92 ethylene-vinyl acetate copolymer (89.3 parts by weight). The blending was carried out by kneading at 130°-150° C. for approximately 20 minutes in a Brabender Plasticorder (®) mixer. Samples of the resultant materials were pressed at approximately 1,000 psi (70 kg/cm) between platens heated to 150° C. Monolayer films of about 3 inches (7.6 cm) by 5 inches (12.7 cm) by 0.005 inch (0.013 cm) were thus obtained. The SDT of each film was determined before and after a 24-hour water shower. The results are summarized below:

TABLE VIB

| Sample | QA | SDT Before Shower (ms) | SDT After Shower (ms) |
|---|---|---|---|
| 1 | QA5 | 490 | 2450 |
| 2 | QA4 | 40 | 1000 |
| 3 | QA1 | 90 | 510 |
| 4 | QA2 | 100 | 880 |

These results demonstrate that the performance of the films tested was slightly degraded by an extensive water shower, but still less than 3000 ms for Sample 1 and less than the preferred 2000 ms for Samples 2, 3, and 4.

Next, several quaternary amines (QA 5.0 parts by weight) were blended with Primacor 1410 ethylene-acrylic acid copolymer (71.3 parts by weight) and LD318.92 ethylene-vinyl acetate copolymer (23.7 parts by weight). The blending and subsequent film preparation and testing were carried out as described above for the samples reported in Table VIB. The results were as follows:

TABLE VIC

| Sample | QA | SDT Before Shower (ms) | SDT After Shower (ms) |
|---|---|---|---|
| 5 | Cyastat LS | 420 | 500 |
| 6 | Larostat 264A | 590 | 630 |
| 7 | QA3 | 110 | 650 |
| 8 | QA1 | 550 | 720 |
| 9 | QA2 | 70 | 180 |

These results demonstrate that there was almost no loss of static decay performance after extensive water washing, and all SDT's were less than the preferred 2000 ms.

To demonstrate further permanence of these materials, the same samples 5 through 9 from after the water shower were further aged for 12 days in an oven at 70° C. and ambient humidity, i.e. a "dry" oven as there was no water beaker. SDT, surface resistivity, and volume resistivity for the resulting films are given below:

TABLE VID

| RESULTS AFTER WATER SHOWER AND 12-DAY AGING AT 70° C. | | | |
|---|---|---|---|
| Sample | SDT (ms) | Surface Resistivity (ohms/square) | Volume Resistivity (ohm-cm) |
| 5 | 1660 | $1.1 \times 10^{13}$ | $4.4 \times 10^{12}$ |
| 6 | 1790 | $4.0 \times 10^{12}$ | $1.3 \times 10^{12}$ |
| 7 | 330 | $3.8 \times 10^{11}$ | $7.7 \times 10^{11}$ |
| 8 | 790 | $4.7 \times 10^{11}$ | $9.1 \times 10^{11}$ |
| 9 | 120 | $3.8 \times 10^{11}$ | $1.1 \times 10^{11}$ |

The results demonstrate that films produced with 5% of a QA additive in an EAA/EVA resin show excellent static decay times, surface resistivities, and volume resistivities, and are highly permanent, i.e., insensitive to water washout of additive and 12-day aging at elevated temperature.

COMPARATIVE EXAMPLE VII

A comparative sample was run for comparison with Sample 5 as reported in Tables VIC and VID above to show the result of omitting the ethylene-acrylic acid copolymer from the formulation. Thus, Cyastat LS (5.0 parts by weight) and LD318.92 ethylene-vinyl acetate copolymer (95.0 parts by weight) were kneaded at 130°–150° C. in a Brabender Plasticorder (®) mixer. Effective mixing of these ingredients was never obtained, even after 4 hours of kneading. Reduction of the additive content to 2.5 parts by weight did not solve the problem. This demonstrates that an acid copolymer containing carboxylic acid moieties (i.e. the ethylene-acrylic acid copolymer) plays a critical role in compatibilizing the polyolefin with the ionic additive.

Another comparative sample was run but this time for comparison with Sample 9 as reported in Tables VIC and VID above to show the result of omitting the ethylene-acrylic acid copolymer from the formulation. Thus, QA2 (1.5 parts by weight) and LD318.92 ethylene-vinyl acetate copolymer (98.5 parts by weight) were kneaded at 130°–150° C. in a Brabender Plasticorder (®) mixer. Effective mixing of these ingredients was obtained, finally after 4 hours of kneading. Some of the resultant material was pressed at approximately 1000 psi (70 kg/cm$^2$) between platens heated to 150° C. Mono-layer film of about 3×5×0.005 inches (7.6×12.7×0.013 cm) was thus obtained. The SDT of each film was determined before and after a 24-hour water shower. The results are summarized below:

TABLE VII

| SDT Before Shower (ms) | SDT After Shower (ms) |
|---|---|
| 580 | over 30000 |

Also, after the water shower, the film held a charge of 10 kilovolts, which indicates the antistatic property was lost. This demonstrates that an acid copolymer containing carboxylic acid moieties (i.e. the ethylene-acrylic acid copolymer) plays a critical role in providing permanent antistatic characteristics, i.e. enabling the film still to have a SDT less than about 3000 ms, more preferably less than about 2000 ms, after a 24-hour water shower.

EXAMPLE VIII

Quaternary amine QA2 (as defined in Table VIA, 6.0 parts) was blended with Surlyn 1650 partially zinc neutralized ethylene-methacrylic acid-zinc methacrylate ionomer (23.5 parts) and LD318.92 ethylene-vinyl acetate copolymer (70.5 parts). The blending and subsequent testing were carried out as described in Example VI. The results were as follows:

| Before Water Shower: | |
|---|---|
| SDT (ms) | 470 |
| Surface Resistivity (ohms/square) | 1.7 × 10$^{12}$ |
| Volume Resistivity (ohm-cm) | 2.5 × 10$^{12}$ |
| After 24-Hour Water Shower: | |
| SDT (ms) | 880 |
| Surface Resistivity (ohms/square) | 7.6 × 10$^{12}$ |
| Volume Resistivity (ohm-cm) | 3.6 × 10$^{10}$ |
| After 24-Hour Water Shower Followed by 12-Day/70° C. Aging: | |
| SDT (ms) | 460 |
| Surface Resistivity (ohms/square) | 1.7 × 10$^{12}$ |
| Volume Resistivity (ohm-cm) | 2.5 × 10$^{12}$ |

These results demonstrate that the film showed excellent static decay time, surface and volume resistivity, and resistance to water washout of additive and aging at elevated temperature.

EXAMPLE IX

Quaternary amine QA1 (5.0 parts) was blended with Surlyn 1650 partially zinc neutralized ethylene-methacrylic acid-zinc methacrylate ionomer (23.7 parts) and LD318.92 ethylene-vinyl acetate copolymer (71.3 parts). The blending and subsequent testing were carried out as described in Example VI. The results were as follows:

| Before Water Shower: | |
|---|---|
| SDT (ms) | 230 |
| Surface Resistivity (ohms/square) | 5.2 × 10$^{11}$ |
| Volume Resistivity (ohm-cm) | 1.4 × 10$^{12}$ |
| After 24-Hour Water Shower: | |
| SDT (ms) | 150 |
| Surface Resistivity (ohms/square) | 6.5 × 10$^{11}$ |
| Volume Resistivity (ohm-cm) | 1.1 × 10$^{12}$ |
| After 24-Hour Water Shower Followed by 12-Day/70° C. Aging: | |
| SDT (ms) | 80 |
| Surface Resistivity (ohms/square) | 5.9 × 10$^{11}$ |
| Volume Resistivity (ohm-cm) | 5.9 × 10$^{12}$ |

These results demonstrate that the film showed excellent static decay time, surface and volume resistivity, and resistance to water washout of additive and aging at elevated temperature.

EXAMPLE X

Quaternary amine QA6, N,N-dimethyl-N-ethyl-N-cocoammonium ethosulfate, was prepared as follows: 9.36 g of N,N-dimethylcocoamine, was combined with 6.10 g of diethyl sulfate. After mixing at 80° C. for 2–3 minutes, a clear liquid was formed in an exothermic process. On cooling, a waxy solid (m.p. 65°–75° C.) resulted (QA6).

Quaternary amine QA6 (4.44 g) was blended with 10 g Dow Primacor 1410 (ethylene-acrylic acid copolymer, 9% AA, 1.5 melt index) and 30 g Exxon LD318.92 (ethylene-vinyl acetate copolymer, 9% VA, 2.0 melt index). Blending was carried out in a Brabender Plasticorder mixer at 130° C. for 30 minutes. A sample of the resultant material was pressed at approximately 1,000 psi (70 kg/cm$^2$) between platens heated to 150° C. A monolayer film of about 3 inches (7.6 cm) by 5 inches (12.7 cm) by 0.005 inch (0.013 cm) was thus obtained.

The surface resistivity of the sample was tested by two methods: First, the sample was equilibrated at 12.5±0.5% RH for 48 hours and tested with a Keithley 6105 resistivity adapter (Keithley Instruments, Cleveland, Ohio) connected to a Keithley 247 high voltage supply and a Keithley 485 picoammeter. With an applied voltage of 100 volts, a surface resistivity of 9.96×10$^9$ ohms/square was obtained. Second, the sample was equilibrated at 35 ±5% for >2 hours and tested with a TREK model 150 resistivity meter (TREK, Inc., Medina, N.Y.). A surface resistivity of 9×10$^7$ ohms/square was obtained.

EXAMPLE XI

Quaternary amine QA6 (4.44 g) was blended with 10 g Surlyn 1650 partially zinc neutralized ethylene-methacrylic acid-zinc methacrylate terpolymer and 30 g Exxon LD318.92 as described in Example X.

When prepared and tested as described in Example X, a film sample of this material gave the following results:

Surface Resistivity after equilibration
at $12.5\pm0.5\%$ RH for 48 hrs.: $2.00\times10^{10}$ ohms/square
Surface Resistivity after equilibration
at $35\pm5\%$ RH $\frac{1}{4}$ 2 hrs.: $2\times10^{8}$ ohms/square

EXAMPLE XII

By blending with heat using a Berstorff twin screw extruder, a premix of pellets was made. First, 60 parts by weight EVA (LD318.92) and 30 parts by weight EAA (Primacor 5981) were mixed, and then added thereto was 20 parts by wt. QA [Emerstat 6660]. The resultant EVA+EAA+QA was then further blended with more polymer, and hot blown, 5-layer, extruded, tubular film having a thickness of about 4 mil (0.102 mm) was made. The ingredients of each layer were as recited in Table XIIA and are in % by weight.

TABLE XIIA

| OUTSIDE LAYER 1 | INTERIOR LAYER 2 | CORE LAYER 3 | INTERIOR LAYER 4 | OUTSIDE LAYER 5 |
|---|---|---|---|---|
| 100% EVA | 100% EVA | 100% LLDPE | 100% EVA | 66⅔% EVA 33⅓% Mix of EVA + EAA + QA |

Then, the following electrical measurements were taken on samples of film as reported in Table XIIB. Resistivity was measured at about $12.5\pm2.5\%$ RH using a Keithley picoammeter with a separate 100 volt power source and an Electro Technical Services cell conforming to ASTM D257.

TABLE XIIB

| Abuse Treatment or Film Tested As is | Ohms/square Surface Resistivity | Ohms-cm Volume Resistivity | Static Decay Time (ms) | | | Tribo Volts |
|---|---|---|---|---|---|---|
| | | | 1 Hr. Equilibration treatment | 24 Hr. Equilibration treatment | 48 Hr. Equilibration treatment | |
| As is | $5.9\times10^{11}$ | $1.8\times10^{16}$ | 1852 | 1824 | NT* | 86 |
| 24 Hr. Shower | $1.9\times10^{14}$ | NT | NT | WON'T ACCEPT FULL CHARGE | WON'T ACCEPT FULL CHARGE | NT |
| Hot Dry Oven | | | | | | |
| Day 1 | NT | NT | 2190 | 1722 | NT | NT |
| Day 2 | NT | NT | 1492 | 3000 | NT | NT |
| Day 3 | NT | NT | 1471 | 1398 | NT | NT |
| Day 4 | NT | NT | 1326 | 1332 | NT | NT |
| Day 5 | NT | NT | 1501 | 1453 | NT | NT |
| Day 6 | NT | NT | NT | NT | NT | NT |
| Day 7 | NT | NT | NT | NT | NT | NT |
| Day 8 | NT | NT | NT | NT | NT | NT |
| Day 9 | NT | NT | NT | NT | NT | NT |
| Day 10 | NT | NT | NT | 1845 | NT | NT |
| Day 11 | NT | NT | NT | 1794 | NT | NT |
| Day 12 | $2.0\times10^{12}$ | $2.3\times10^{16}$ | NT | 15940 | NT | 537 |

*NT = not tested

These results illustrate that after 11 days in a hot oven, the film exhibited an excellent SDT less than 2000 ms.

EXAMPLE XIII

By blending with heat using a Berstorff twin screw extruder, a premix of pellets was made. First, 60 parts by weight EVA [LD318.92] and 30 parts by weight EAA [Primacor 5981] were mixed, and then added thereto was 20 parts by wt. QA [Emerstat 6660]. The resultant mix of EVA+EAA+QA was then further blended with more polymer, and hot blown, 5-layer extruded, tubular film having a thickness of about 4 mil (0.102 mm) was made. The ingredients of each layer were as recited in Table XIIIA and are in % by weight.

TABLE XIIIA

| OUTSIDE LAYER 1 | INTERIOR LAYER 2 | CORE LAYER 3 | INTERIOR LAYER 4 | OUTSIDE LAYER 5 |
|---|---|---|---|---|
| 66⅔% Primacor 1410 33⅓% Mix of EVA + EAA + QA | 66⅔% EVA 33⅓% Mix of EVA + EAA + QA | 100% LLDPE | 66⅔% EVA 33⅓% Mix of EVA + EAA + QA | 66⅔% Prmacor 1410 33⅓% Mix of EVA + EAA + QA |

Then, the following electrical measurements were taken on samples of film as reported in Table XIIIB. Resistivity was measured at about $12.5\pm2.5\%$ RH using a Keithley picoammeter with a separate 100 volt power source and an Electro Technical Services cell conforming to ASTM D257.

TABLE XIIIB

| Abuse Treatment or Film Tested As is | Ohms/square Surface Resistivity | Ohms-cm Volume Resistivity | Static Decay Time (ms) 1 Hr. Equilibration treatment | 24 Hr. Equilibration treatment | 48 Hr. Equilibration treatment | Tribo Volts |
|---|---|---|---|---|---|---|
| As is | $1.3 \times 10^{11}$ | $5.1 \times 10^{13}$ | 40 | 80 | NT* | 47 |
| 24 Hr. Shower | $7.9 \times 10^{11}$ | NT | NT | 109 | 108 | NT |
| Hot Dry Oven | | | | | | |
| Day 1 | NT | NT | 217 | 185 | NT | NT |
| Day 2 | NT | NT | 130 | 181 | NT | NT |
| Day 3 | NT | NT | 68 | 64 | NT | NT |
| Day 4 | NT | NT | 73 | 84 | NT | NT |
| Day 5 | NT | NT | 86 | 88 | NT | NT |
| Day 6 | NT | NT | 107 | NT | NT | NT |
| Day 7 | NT | NT | NT | NT | NT | NT |
| Day 8 | NT | NT | NT | NT | NT | NT |
| Day 9 | NT | NT | NT | NT | NT | NT |
| Day 10 | NT | NT | NT | 84 | NT | NT |
| Day 11 | NT | NT | NT | 94 | NT | NT |
| Day 12 | $1.6 \times 10^{11}$ | $2.1 \times 10^{13}$ | NT | 51 | NT | 56 |

*NT = not tested

These results illustrate that after a 24-hour water shower and also after 12 days in a hot oven, the film exhibited both a permanent antistatic SDT less than 2000 ms and a permanent surface resistivity in the antistatic surface resistivity range of $10^5$ to $10^{12}$ ohms/square.

EXAMPLE XIV

By blending with heat using a Berstorff twin screw extruder, a premix of pellets was made. First, 60 parts by weight EVA [LD318.92] and 30 parts by weight EAA [Primacor 5981] were mixed, and then added thereto was 20 parts by wt. QA [Emerstat 6660]. The resultant mix of EVA+EAA+QA was then further blended with more polymer, and hot blown, 5-layer, extruded, tubular film having a thickness of about 4 mil (0.102 mm) was made. The ingredients of each layer were as recited in Table XIVA and are in % by weight.

TABLE XIVA

| OUTSIDE LAYER 1 | INTERIOR LAYER 2 | CORE LAYER 3 | INTERIOR LAYER 4 | OUTSIDE LAYER 5 |
|---|---|---|---|---|
| 56⅔% Primacor 1410 33⅓% Mix of EVA + EAA + QA 10% Antiblock | 66⅔% EVA 33⅓% Mix of EVA + EAA + QA | 100% LLDPE | 66⅔% EVA 33⅓% Mix of EVA + EAA + QA | 56⅔% Primacor 1410 33⅓% Mix of EVA + EAA + QA 10% Antiblock |

Then, the following electrical measurements were taken on samples of film as reported in Table XIVB. Resistivity was measured at about 12.5±2.5% RH using a Keithley picoammeter with a separate 100 volt power source and an Electro Technical Services cell conforming to ASTM D257.

TABLE XIVB

| Abuse Treatment or Film Tested As is | Ohms/square Surface Resistivity | Ohms-cm Volume Resistivity | Static Decay Time (ms) 1 Hr. Equilibration treatment | 24 Hr. Equilibration treatment | 48 Hr. Equilibration treatment | Tribo Volts |
|---|---|---|---|---|---|---|
| As is | $1.2 \times 10^{11}$ | $5.8 \times 10^{13}$ | 11 | 31 | NT* | 35 |
| 24 Hr. Shower | $6.6 \times 10^{11}$ | NT | NT | 70 | 62 | NT |
| Hot Dry Oven | | | | | | |
| Day 1 | NT | NT | 40 | 26 | NT | NT |
| Day 2 | NT | NT | 42 | 32 | NT | NT |
| Day 3 | NT | NT | 41 | 40 | NT | NT |
| Day 4 | NT | NT | 36 | 33 | NT | NT |
| Day 5 | NT | NT | 52 | 42 | NT | NT |
| Day 6 | NT | NT | 53 | NT | NT | NT |
| Day 7 | NT | NT | NT | NT | NT | NT |
| Day 8 | NT | NT | NT | NT | NT | NT |
| Day 9 | NT | NT | NT | NT | NT | NT |
| Day 10 | NT | NT | NT | 45 | NT | NT |
| Day 11 | NT | NT | NT | 44 | NT | NT |
| Day 12 | $1.6 \times 10^{11}$ | $2.4 \times 10^{13}$ | NT | 65 | NT | 35 |

*NT = not tested

These results illustrate that after a 24-hour water shower and also after 12 days in a hot oven, the film exhibited both a permanent antistatic SDT less than 2000 ms and a permanent surface resistivity in the antistatic surface resistivity range of $10^5$ to $10^{12}$ ohms/square.

From the foregoing description, one skilled in the art can easily ascertain the essential characteristics of this invention, and without departing from the spirit and scope thereof, can make various changes and modifications of the invention to adapt it to various usages and conditions.

What we claim is:

1. An antistatic film comprising an acid copolymer/quaternary amine mixture of (A) a polymer containing carboxylic acid moieties and (B) an antistatically effective amount of a quaternary amine wherein:

(A) the polymer containing carboxylic acid moieties is a copolymer of (i) a major amount by mol % of an alpha-olefin of the formula $RCH=CH_2$ wherein R is H or $C_1$ to $C_8$ alkyl, and (ii) a minor amount by mol % of an alpha,beta-ethylenically unsaturated carboxylic acid, and (B) the quaternary amine is of the formula

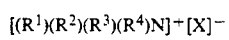

wherein $R^1$ is selected from H, aryl, or $C_1$ to $C_{50}$ alkyl optionally having one or more non-contiguous $C=O$ or $NHC=O$ or $-S-$ or $-O-$ in the carbon chain, or the same as $R^2$;

each of $R^2$, $R^3$, and $R^4$ is the same or different and selected from H, $C_1$ to $C_{18}$ alkyl optionally substituted with one or more OH or from $-(R^5-O)_a-H$ where a is an integer from 1 to 10 and $R^5$ is ethylene or propylene; and X is an anion selected from chloride, bromide, iodide, fluoride, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, trifluoroacetate, citrate, propionate, tartrate or carbonate, wherein said film is permanently antistatic, and wherein said film has three layers, each containing a mixture of (A) and (B).

2. An antistatic film comprising an acid copolymer/quaternary amine mixture of (A) a polymer containing carboxylic acid moieties and (B) an antistatically effective amount of a quaternary amine wherein:

(A) the polymer containing carboxylic acid moieties is a copolymer of (i) a major amount by mol % of an alpha-olefin of the formula $RCH=CH_2$ wherein R is H or $C_1$ to $C_8$ alkyl, and (ii) a minor amount by mol % of an alpha, beta-ethylenically unsaturated carboxylic acid, and (B) the quaternary amine is of the formula

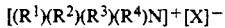

wherein $R^1$ is selected from H, aryl, or $C_1$ to $C_{50}$ alkyl optionally having one or more non-contiguous $C=O$ or $NHC=O$ or $-S-$ or $-O-$ in the carbon chain, or the same as $R^2$;

each of $R^2$, $R^3$, and $R^4$ is the same or different and selected from H, $C_1$ to $C_{18}$ alkyl optionally substituted with one or more OH or from $-(R^5-O)_a-H$ where a is an integer from 1 to 10 and $R^5$ is ethylene or propylene; and X is an anion selected from chloride, bromide, iodide, fluoride, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, trifluoroacetate, citrate, propionate, tartrate or carbonate, wherein said film is permanently antistatic, and wherein said film has three layers, each containing a mixture of (A) and (B), and wherein said film is oriented.

3. An antistatic film comprising an acid copolymer/quaternary amine mixture of (A) a polymer containing carboxylic acid moieties and (B) an antistatically effective amount of a quaternary amine wherein:

(A) the polymer containing carboxylic acid moieties is a copolymer of (i) a major amount by mol % of an alpha-olefin of the formula $RCH=CH_2$ wherein R is H or $C_1$ to $C_8$ alkyl, and (ii) a minor amount by mol % of an alpha,beta-ethylenically unsaturated carboxylic acid, and (B) the quaternary amine is of the formula

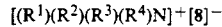

wherein $R^1$ is selected from H, aryl, or $C_1$ to $C_{50}$ alkyl optionally having one or more non-contiguous $C=O$ or $NHC=O$ or $-S-$ or $-O-$ in the carbon chain, or the same as $R^2$;

each of $R^2$, $R^3$, and $R^4$ is the same or different and selected from H, $C_1$ to $C_{18}$ alkyl optionally substituted with one or more OH or from $-(R^5-O)_a-H$ where a is an integer from 1 to 10 and $R^5$ is ethylene or propylene: and X is an anion selected from chloride, bromide, iodide, fluoride, nitrate, fluoborate, phosphate, $C_1$ to $C_8$ alkyl phosphate, sulfate, $C_1$ to $C_8$ alkyl sulfate, formate, $C_1$ to $C_8$ alkyl or $C_6$ to $C_{24}$ alkaryl or aryl sulfonate, acetate, trifluoroacetate, citrate, propionate, tartrate or carbonate, wherein said film is permanently antistatic, and wherein said film has a core layer containing a mixture of (A) and (B), and two surface layers, each of said surface layers being free of a mixture of (A) and (B), and wherein said film is oriented.

* * * * *